United States Patent [19]

Dorai et al.

[11] Patent Number: 5,118,869
[45] Date of Patent: Jun. 2, 1992

[54] POLYMERIZING TETRAHYDROFURAN TO PRODUCE POLYTETRAMETHYLENE ETHER GLYCOL USING A MODIFIED FLUORINATED RESIN CATALYST CONTAINING SULFONIC ACID GROUPS

[75] Inventors: Suriyanarayan Dorai, Lockport, N.Y.; Gerfried Pruckmayr, Media, Pa.; Marianne Marsi, Wilmington, Del.; Willard L. Quon, East Amherst, N.Y.

[73] Assignee: E. I. Du Pont de Nemours and Company, Wilmington, Del.

[21] Appl. No.: 654,496

[22] Filed: Feb. 13, 1991

[51] Int. Cl.$^5$ ............................................. C07C 41/01
[52] U.S. Cl. ..................................................... 568/617
[58] Field of Search ......................................... 568/617

[56] References Cited

U.S. PATENT DOCUMENTS 4,163,115  7/1979  Heinsohn et al. .................. 560/240
4,202,964  5/1980  Pruckmayr et al. ................ 568/617

*Primary Examiner*—Howard T. Mars

[57] ABSTRACT

A catalyst and process for preparing it and its use in polymerizing tetrahydrofuran to produce polytetramethylene ether glycol ether are disclosed. The catalyst is a blend of a fluorinated resin containing sulfonic acid groups and a fluorinated resin containing carboxylic acid groups. The catalyst is partially dried to contain from 1,000 to 2,000 ppm water, so that when it is used to polymerize tetrahydrofuran, the product polytetramethylene ether glycol will have a number average molecular weight of from 250 to 4,000.

10 Claims, No Drawings

POLYMERIZING TETRAHYDROFURAN TO PRODUCE POLYTETRAMETHYLENE ETHER GLYCOL USING A MODIFIED FLUORINATED RESIN CATALYST CONTAINING SULFONIC ACID GROUPS

FIELD OF THE INVENTION

The present invention relates to an improved process for producing polytetramethylene ether glycol from tetrahydrofuran using a catalyst which is a fluorinated resin containing both sulfonic acid groups and carboxylic acid groups or a blend of fluorinated resin containing sulfonic acid groups and a fluorinated resin containing carboxylic acid groups. An important aspect of the present invention involves activating the sulfonic acid groups containing fluorinated resin prior to its use as catalyst. This activation involves a partial dehydration of the catalyst to contain from not more than 1,000 to 2,000 ppm (0.1 to 0.2 wt. %) water. Further, the catalytic resin may be blended with one or more other resins to control its catalytic activity.

BACKGROUND OF THE INVENTION

Poly(tetramethylene ether) glycol (PTMEG) is a commodity in the chemical industry, widely used in the manufacture of block copolymers in combination with polyfunctional urethanes and polyesters such as polybutylene terephthalate. It is commonly prepared by reaction of tetrahydrofuran (THF) with a strong acid catalyst such as fluorosulfonic acid and then quenching and hydrolyzing the product with water.

While this process has proved to be quite satisfactory, it is not as efficient as desired because the acid catalyst cannot be recovered and reused again. Moreover, disposal of the spent acid is a problem because of its toxicity and corrosiveness.

U.S. Pat. No. 4,120,903 describes the preparation of PTMEG by the polymerization of THF using, as catalysts, perfluorinated ion-exchange polymers with pendant sulfonic acid groups (PFIEP-$SO_3H$) which have a low enough solubility to allow easy separation from the product, thus permitting their reuse. A method for avoiding the disposal problem traditionally associated with the strong acid catalyst was therefore possible based on the reaction equations (1) through (4) of U.S. Pat. No. 4,120,903, Column 1, where P-$SO_3H$ has the same meaning as PFIEP-$SO_3H$ herein. The PFIEP-$SO_3H$ catalyst is further described by F. J. WALLER and R. W. Van Scoyoc, CHEMTECH, Jul., 1987, pages 438–441.

There are two drawbacks to implementation of this technology, however, in that (1) the polymerization is sensitive to moisture necessitating that both the catalyst and the THF be specially dried before use and (2) the PTMEG made using this process had a number average molecular weight 10,000 or greater.

One approach to circumvent these drawbacks by Heinson et al using the PFIEP-$SO_3H$ catalyst of U.S. Pat. No. 4,120,903 above is disclosed in U.S. Pat. No. 4,163,115. This patent discloses maintaining an anhydrous reaction environment by carrying out the polymerization of terahydrofuran in the presence of an acylium ion precursor, i.e. a carboxylic acid anhydride such as acetic anhydride and optionally the corresponding carboxylic acid. Esters of the PTMEG were formed with facile control of molecular weight in the desired commercial range or up to very high molecular weights. Recovery of the PTMEG, however, required saponification or methanolysis, and thereby diminishing the advantages of this process.

An insoluble catalyst, less sensitive to moisture in the polymerization system, and which could yield commercial grade PTMEG in the desired molecular weight ranges of 250 to 4,000 would have a distinct advantage.

The present invention is an improvement in the process for PTMEG manufacture within the commercially important molecular weight range of 250 to 4,000 in which THF containing the amount of water usually found in commercial polymerization-grade material, and an insoluble catalyst are brought together under conditions suitable for polymerization. After the desired polymerization has taken place, the catalyst may be separated from the bulk of the reaction mass for reuse and the PTMEG isolated by the usual methods. Part of the water introduced into the system either with the catalyst or the THF, acts as the chain terminator for the polymerization and, as such, is consumed. The catalyst of this invention is a blend of a perfluorinated ion exchange polymer containing pendant sulfonic acid groups (PFIEP-$SO_3H$) with a perfluorinated ion exchange polymer containing pendant carboxylic acid groups (PFIEP-$CO_2H$). The PFIEP-$SO_3H$/PFIEP-$CO_2H$ may be used as is or it may be further blended with other, inert polymers before use. Ordinarily, these catalysts would not yield commercial grade PTMEG in the desired molecular weight range from 250 to 4,000 largely due to the poor access of the active sulfonic acid end groups to THF. The accessibility is considerably improved by swelling the catalyst in THF after activation by partial dehydration through (1) heating to 90° C. or (2) by leaching the catalyst with dry THF or (3) drying the catalyst using a dehydrating agent like trimethyl orthoformate or (4) by distilling off the water contained in the catalyst or through any combination of the above methods.

SUMMARY OF THE INVENTION

10 The catalyst of this invention is a blend of perfluorinated ion exchange polymer containing pendant sulfonic acid groups (PFIEP-$SO_3H$) with a perfluorinated ion exchange polymer containing pendant carboxylic acid groups (PFIEP-$CO_2H$). Activating this catalyst is an extremely important step in preparing the desired low molecular weight PTMEG. The activity of the catalyst is improved sufficiently by partial dehydration by either (1) heating to 90° C. for a period of time sufficient to reduce water content to a critical level, (2) leaching the catalyst with dry THF, or (3) drying the catalyst using a dehydrating agent, trimethyl orthoformate for example, or (4) by distilling off the water contained in the catalyst or through any combination of the above methods.

The polymerization process may be run either batchwise or continuously. Water input is monitored since it is a chain terminating agent and its levels affect the molecular weight of the product PTMEG. After the reaction mass is removed from the reactor, the unreacted THF and catalyst are removed by conventional means to yield the PTMEG product.

DETAILED DESCRIPTION OF THE INVENTION

The catalyst of this invention is a blend of PFIEP-$SO_3H$ and PFIEP-$CO_2H$ formed by blending a melt-fabricable first polymer having sulfonyl functional groups and a melt-fabricable second polymer having carboxylic functional groups, hydrolyzing the functional groups to ionizable functional groups, and finally, if base has been used for the hydrolysis, acidifying the ionizable functional groups to the corresponding sulfonic and carboxylic acid groups.

The melt-fabricable first polymer having sulfonyl functional groups is typically a polymer having a fluorinated hydrocarbon backbone chain to which are attached the functional groups or pendant side chains which in turn carry the functional groups. The pendant side chains can contain, for example,

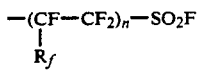

groups, wherein $R_f$ is F, Cl, or a C-1 to C-10 perfluoroalkyl radical and n is an integer from 1 to 5. Ordinarily, the functional group in the side chains of the polymer will be present in terminal

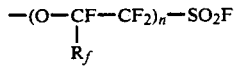

groups where $R_f$ and n have the meanings defined above. Examples of fluorinated polymers of this kind are disclosed in U.S. Pat. Nos. 3,282,875, 3,560,568, 3,718,627, 4,417,969 and 4,610,762.

The melt-fabricable second polymer having carboxylic functional groups is typically a polymer having a fluorinated hydrocarbon backbone chain to which are attached the functional groups or pendant side chains which carry the functional groups. The pendant side chains can contain, for example,

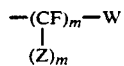

groups, wherein Z is F or $CF_3$, m is 1 to 12, and W is $-COOR$, $-CF_2COOR$ or $-CN$, wherein R is lower alkyl. Ordinarily, the functional group in the side chains of the polymer will be present in terminal

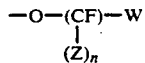

groups. Examples of fluorinated polymers of this kind are disclosed in British Patent No. 1,145,445 and U.S. Pat. No. 3,506,635.

The first and second polymers are then blended as described for example in U.S. Pat. No. 4,176,217, Col. 7, lines 43–55 and Example 1. The resulting blend is then extruded into film or pellet form, hydrolyzed with base, and then acidified to give a blend of PFIEP-SO$_3$H and PFIEP-CO$_2$H. Techniques for hydrolyzing and subsequently acidifying the ionizable functional groups of these polymers are described in U.S. Pat. No. 4,176,215, Col. 9 lines 25–45 and Example 1.

The catalysts of this invention can be used as is or blended with one or more inert polymers prepared from ethylenically unsaturated monomers. Examples of such monomers are ethylene, styrene, vinyl chloride, vinyl fluoride, vinylidene fluoride, chlorotrifluoroethylene, vinyl ethers, perfluoroalkyl vinyl ethers, tetrafluoroethylene, hexafluoropropylene, or combinations thereof. The solid blends of the polymers of this invention, containing preferably about 20 to 80% of the inert diluent polymer, can be prepared by techniques familiar in the art. Powders, granules or pellets of the individual polymers can first be mixed together. Such a mixture is then subjected to heat and pressure by various means, such as pressing, extruding in a screw extruder, or working on a roll mill or rubber mill. To insure formation of an intimate uniform blend, the steps can be repeated two or more times. For example, pressed films can be flaked or cut into small pieces and repressed into film. Extruded polymer can be chopped into pellets as it is extruded, and then re-extruded. Powders for blending can be made by grinding in a mill; cold grinding in a freezer mill is also a useful technique.

A suitable catalyst for use in this invention is a blend of 40–95% PFIEP-SO$_3$H and 60–5% PFIEP-CO$_2$H. The preferred catalyst is a blend of 70–95% PFIEP-SO$_3$H and 30–5% PFIEP-CO$_2$H. The PFIEP-CO$_2$H component can also be replaced with an inert filler like polytetrafluoroethylene, polychlorotrifluoroethylene or copolymers of either of these with hexafluoropropylene or a perfluoroalkyl vinyl ether wherein the alkyl groups contain from 1 to 6 carbon atoms, or any combination thereof.

Catalyst activation is an extremely important step in preparing the desired low molecular weight PTMEG. Unactivated catalyst, when used for polymerizing THF, usually results in production of PTMEG having molecular weight greater than 10,000. The catalyst can be activated by any one or a combination of the following methods:

(1) The catalyst is first dried in an oven at about $\sim 100°$ C. for about 8 hours under reduced pressure ranging between 0.1–100 mm mercury. The catalyst is then mixed with THF containing 50 to 300 ppm water and the slurry heated under nitrogen pressure at 85° C. or higher for at least three hours. The preferred range of activation temperatures is 85–150° C. and the hold-up time should be at least 3 hours. This type of activation is useful because THF does not polymerize under these conditions. It is thermodynamically impossible to polymerize THF at temperatures greater than 85° C. One plausible explanation for catalyst activation is the fact that the bulk of water present in the system is vaporized at these temperatures thereby dehydrating the catalyst.

(2) The catalyst is leached with dry THF (water concentration <100 ppm) several times at temperatures ranging between 0° and 90° C. Each time the catalyst is leached with THF, the water concentration in the catalyst decreases. The most active catalyst is produced by leaching with THF until water concentration in THF is reduced to below 100 ppm. The estimated water concentration in the leached catalyst is about $\sim 2000$ ppm.

(3) The catalyst is dried in an oven at 140–180° C. in a vacuum oven maintained at 0.1–10 mm mercury in the presence of trimethyl orthoformate (TMOF). The ratio of trimethyl orthoformate to the catalyst ranges between 0.5–50 by weight. The trimethyl orthoformate reacts with water present in the catalyst to produce methyl formate and methanol both of which are highly volatile. The catalyst is treated in several stages with TMOF, (Total amount of TMOF used is 0.5–50 times the amount of catalyst). The catalyst is then dried under the same conditions as above in a vacuum oven for 8 hours to ensure the unreacted TMOF along with the volatile reaction product are removed. The water concentration in the dehydrated catalyst is about 1000-2000 ppm. The dehydrated catalyst is cooled and ready to use for polymerizing THF. (4) The catalyst is dried by distilling off the water in the presence of THF. The wet catalyst is mixed with THF and the THF/water mixture distilled off either by heating at the normal boiling point of the solution at atmospheric pressure or by vacuum distillation at lower temperatures ranging between 0°-60° C. The amount of THF distilled and used in this process ranges from 10 to 20 times the weight of the catalyst, depending on initial moisture content of the catalyst. The catalyst contains from 1000 to 2000 ppm of residual water following this treatment and is active enough to be used as is without further activation.

The THF used for polymerization can be any of those commercially available for polymerization. Its water content usually varies between 10 and 1000 ppm. The peroxide content is normally less than 0.002% by weight. The THF may optionally contain a oxidation inhibitor such as butylated hydroxytoluene to prevent formation of undesirable color or excess peroxides. The type and concentration of the inhibitor have little or no effect on the polymerization.

The water contained in the system of this invention acts as the chain terminator for the polymerization and, as such, its concentration is important since it has an effect on the number-average molecular weight of the product PTMEG. The less water present the higher the average molecular weight. The more water present, the lower the molecular weight. If too much water is present the propagation rate is very slow. For these reasons, attention must be given to the water content of the system. Water enters the system either with the THF or the catalyst. As stated above, polymerization-grade THF usually contains about 0.001 to 0.1% water. The catalyst also contains water presumably as tightly held hydrates of the strongly acidic sulfonic acid groups. Even after the catalyst has been vacuum dried under stringent conditions, it is estimated that it still may contain up to about 0.2% water by weight. During reaction, water is removed from the system by being consumed as the chain terminator. Because of the above factors, it may be necessary, as processing proceeds and equilibrium conditions are approached, to adjust the water content of the THF being fed to the reactor system to maintain a relatively steady molecular weight in the desired range, from batch to batch.

The process of this invention can be run batchwise or continuously:

When run batchwise, a closed reaction vessel purged with a slow flow of dry nitrogen and fitted with an agitator is charged with THF and about 5 to 45%, preferably about 25 to 40%, by weight of the THF, of catalyst which has been activated by one or several combinations of the activation methods described above. The reaction mass is then held, with stirring or agitation, at a temperature ranging from ambient to the boiling point of THF, preferably at 0° to 65° C. If higher temperatures are desired, the reaction can be run under pressure. When the desired degree of polymerization has been reached, generally after 2 to 60 hours, the catalyst can be removed by filtration, centrifugation or decantation, and again dried, if necessary, before reuse.

The progress of the polymerization can be monitored by periodic sampling and analysis by, for example, gel permeation chromatography or by determination of the hydroxyl number.

When run continuously, the THF containing small amounts of chain-terminating water, and optionally the catalyst, also containing small amounts of water, are continuously fed into a reactor at rates which provide the requisite concentrations and suitable residence time, and product and excess reactants are continuously removed. Preferably, the catalyst is charged initially and is held in the reaction zone by suitable screens or filters, and can remain in continuous use. Reactor hold-up-times used in the continuous system range from 4 to 40 hours, operating at temperatures ranging from 5° to 70° C., using a feed rate to the reactor of 0.1 to 1.0 g THF per g of catalyst per hour.

After the reaction mass is withdrawn from the reactor, whether the reactor be batch or continuous, the unreacted THF and catalyst are recovered for recycle by conventional techniques to yield the PTMEG product.

If the catalyst loses its activity over a period of time it may be reactivated by one or several methods of activation outlined above.

Examples of batch and continuous polymerization experiments follow.

EXAMPLE 1

(a) A batch of pelletized (approximately 0.2 mm diameter × 0.5 mm long cylindrical) ion exchange resin blend designated NR-55 containing 78% PFIEP-SO$_3$H and 22% PFIEP-CO$_2$H by weight was activated by leaching with THF repeatedly until the water content of the THF was <80 mcg (micrograms water/mL THF). Leaching was carried out at 20° C. and the activated catalyst was kept soaked in THF for 5 hours.

(b) A 45 g portion of the virgin catalyst as prepared in (a) above and 90.0 g THF were added to a glass-ware batch reactor, and heated to 85° C. for 14 hours to initiate the polymerization. The reactor was then cooled to 2° C. to allow propagation. After 1 hour at 2° C. there was 7.0% conversion to PTMEG with a number average molecular weight ($M_n$) of 550. At the end of 2nd hour the conversion reached 8.2% at $M_n$ 911. At the end of the 3rd hour conversion increased to 10.6% at $M_n$ 933. After 4 hours and 14.05% conversion to $M_n$ 940, the water concentration had increased to 99 mcg.

The catalyst was rinsed with dry THF, 0.15 g water was added to the reactor, and on the next day Recycle 1 of the same catalyst charge with 90 g new THF was started after heating to 85° C. for 4.5 hours to reinitiate the polymerization.

The above data are reported in the following TABLE 1 extended through four recycles of the same catalyst charge:

TABLE 1

PERFORMANCE OF RESIN CATALYST IN POLYMERIZATION OF THF TO PTMEG

| CATALYST | INITIATION °C./hrs. | PROPIGATION °C./End hr/Conv./$M_n$ | WATER CONC. mcg, and TREATMENT AT END |
|---|---|---|---|
| Virgin | 85/14.0 | 2/1st hr/7.0%/550 | 99 mcg |
| | | 2nd hr/8.2%/911 | Rinsed THF. |
| | | 3rd hr/10.6%/933 | Added 0.15 g |
| | | 4th hr/14.0%/940 | water. |
| Recycle 1 | 85/4.5 | 2/2nd hr/7.0%/931 | 130 mcg |
| | | 3rd hr/13.9%/965 | Rinsed THF. |
| | | 4th hr/14.0%/961 | Added 0.25 g water. |
| Recycle 2 | 85/11.0 | 2/2nd hr/2.0%/250 | 571 mcg High H$_2$O/ |

TABLE 1-continued

PERFORMANCE OF RESIN CATALYST IN POLYMERIZATION OF THF TO PTMEG

| CATA-LYST | INITIATION °C./hrs. | PROPIGATION °C./End hr/Conv./$M_n$ | WATER CONC. mcg. and TREATMENT AT END |
|---|---|---|---|
| Recycle 3 | 85/18.0 | 2/1st hr/7.0%/866<br>2nd hr/13.32/864<br>3rd hr/16.9%/882<br>4th hr/23.3%/896<br>5th hr/27.0%/936<br>6th hr/30.0%/949<br>7th hr/2%/350 | low Mn. Rinsed dry THF. 395 mcg Product lost after 6th hr. Rinsed dry THF. |
| Recycle 4 | 85/14.0 | 2/1st hr/7.5%/890<br>2nd hr/14.5%/905 | Terminated |

EXAMPLE 2

Another sample of 78% PFIEP-SO₃H, 28% PFIEP-CO₂H as used in EXAMPLE 1 (a) above was acid treated and repeatedly rinsed with THF until the water concentration was 92 mcg. This virgin catalyst (39 g) and 77.0 g of dry THF were charged to the batch reactor and heated to 85° C. for 20.0 hours to initiate the polymerization. Next, the reactor and its contents were cooled to 2° C. for the propagation step of the reaction. After the 1st hour, 2.0% conversion to PTMEG with $M_n$ 2300 was found; after the 2nd hour, 7.9% conversion and $M_n$ 2300 were measured; and after the 3rd hour, 6.0% conversion and $M_n$ 2227.

EXAMPLE 3

A 31.0 g sample of 78% pFIEp-SO₃H, 28% PFIEP-CO₂H catalyst as used in EXAMPLES 1 (a) and 2 above was soaked in water, dried at 20° C., and leached with dry THF. The virgin catalyst was added to 63.4 g THF, heated to 85° C. for 19.5 hours to initiate the polymerization, and cooled to 7° C. for propagation. After 1 hour, 10.0% conversion to PTMEG of 1400 $M_n$ resulted.

EXAMPLE 4

A 32.0 g portion of 78% PFIEP-SO3H, 28% PFIEP-CO2H catalyst as used in the above EXAMPLES was leached with dry THF until its water content was mcg. The virgin catalyst and 64.0 g of THF were heated to 86° C. for 12.0 hours to initiate the polymerization and cooled to 54° C. for propagation. Results are reported in the following TABLE 2:

TABLE 2

PERFORMANCE OF RESIN CATALYSTS IN POLYMERIZATION OF THF TO PTMEG

| CATA-LYST | INITIATION °C./hrs. | PROPAGATION °C./End hr/Conv./$M_n$ | WATER CONC. mcg, AND TREATMENT AT END |
|---|---|---|---|
| Virgin | 86/12.0 | 54/1st hr/2.3%/2800<br>2nd hr/5.1%/2800<br>3rd hr/4.0%/2800 | —<br><br>Catalyst rinsed THF |
| Recycle 1 | 85/12.0 | 53/1st hr/7.8%/2800<br>2nd hr/10.7%/2800 | Catalyst rinsed THF |
| Recycle 2 | 85/3.5 | 54/1st hr/2.6%/2800<br>2nd hr/5.0%/2800 | Catalyst rinsed THF |
| Recycle 3 | 85/12.0 | 54/1st hr/8.7%/2800<br>2nd hr/7.7%/2800 | 204 mcg Catalyst rinsed THF |
| Recycle 4 | 85/4.5 | 54/1st hr/4.0%/2300 | Catalyst rinsed THF |
| Recycle 5 | 85/12.0 | 54/1st hr/6.0%/2500 | 120 mcg Catalyst rinsed THF |
| Recycle 6 | 85/12.0 | 55/No data collected | Catalyst rinsed THF |
| Recycle 7 | 85/12.0 | 55/No data collected | Catalyst rinsed THF |
| Recycle 8 | 85/12.0 | 55/1st hr/4.6%/2500 | 245 mcg Catalyst rinsed THF |
| Recycle 9 | 85/12.0 | 60/added 0.5 g 1,4-butane diol<br>1st hr/3.4%/2000<br>4th hr/10.8%/1400 | Catalyst rinsed THF |
| Recycle 10 | 85/12.0 | 60/1.5 hr/9.8%/1400<br>8th hr/9.8%/1400 | Catalyst rinsed THF |
| Recycle 11 | 85/12.0 | 56/1st hr/12.3%/2300<br>7th hr/13.3%/2300 | Catalyst rinsed THF |
| Recycle 12 | 85/12.0 | 55/1st hr/11.5%/2500 | 115 mcg Catalyst rinsed THF |
| Recycle 13 | 85/12.0 | 55/0.5th hr/14.5%/2800<br>1st hr/18.2%/2800 | Added 0.5 g 1,4-butane diol. Catalyst rinsed THF |
| Recycle 14 | 85/18.0 | 65/1st hr/6.0%/2050<br>3rd hr/6.0%/2050 | 119 mcg Catalyst rinsed THF |
| Recycle 15 | 85/4.0 | 65/0.5th hr/5.3%/2000<br>1st hr/6.6%/2000 | NO THF CATALYST RINSE |
| Recycle 16 | 85/12.0 | 65/1st hr/5.8%/2050<br>50/2nd hr/4.9%/2000 | 128 mcg Catalyst rinsed THF |
| Recycle 17 | 85/15.0 | 55/1st hr/4.8%/2500<br>2nd hr/3.9%/2500 | Catalyst rinsed THF |
| Recycle 18 | 90/12.0 | 60/0.5th hr/10.62%/2500<br>1st hr/16.8%/2500<br>2nd hr/18.0%/2500 | 113 mcg<br><br>Catalyst rinsed THF |
| Recycle 19 | 120/12.0 | 60/Catalyst charred by lack of agitation at 120° C. for 12 hrs. Reaction terminated. | |

EXAMPLES 5 through 8 used a catalyst made from a blend of 80% by weight PFIEP-SO₃H and 20% PFIEP-CO₂H. The PFIEP-SO₃H precursor resin used had a melt index of 11. EXAMPLES 5 through 7 were normal particle size: 0.1 diameter × 0.5 mm long cylindrical pellets. The particle size of the catalyst used in EXAMPLE 8 was reduced by approximately one-half. The catalyst of EXAMPLE 9 was made from a blend of 80% by weight PFIEP-SO₃H and 20% fluorinated ethylene propylene polymer (FEP) of the normal particle size, and dried by extraction with THF in the usual manner.

The catalyst for EXAMPLES 5 and 6 started with 70.0 g of resin leached with dry THF at 45° to 50° C. several times until the water concentration in the THF was 166 mcg. The catalyst slurry was divided into approximately equal portions containing 35 g of catalyst and 70 g of THF. The same 35:70 weight ratio of Catalyst to THF was also maintained in EXAMPLE 7. The ratio varied from 35:100 to 35:72-76 for EXAMPLE 8, and was 32:65 in EXAMPLE 9.

In EXAMPLE 5 the catalyst slurry was charged to a glass reactor; in EXAMPLE 6 the reactor was made of steel.

In EXAMPLES 7 and 8 the catalyst was prepared by acid exchange followed by rinsing with dry THF at 21° C. until water in the THF was 74 mcg.

Performance of these catalysts in polymerization of THF to PTMEG is reported in TABLE 3 below.

TABLE 3

RESIN CATALYST PERFORMANCE IN POLYMERIZATION OF THF TO PTMEG

| CATA-LYST | INITIATION °C./hrs. | PROPAGATION °C./End hr/ CONV/$M_n$ | WATER CONC. AT END, mcg |
|---|---|---|---|
| EXAMPLE 5 (Glass Reactor) | | | |
| Virgin | 90/12.0 | Heater to constant temperature bath failed; incomplete initiation. | |
| Recycle 1 | 90/2.0 | 63/1st hr/1.8%/2200 2nd hr/2.2%/2200 | 164 mcg |
| EXAMPLE 6 (Steel Reactor) | | | |
| Virgin | 90/12.0 | Heater to constant temperature bath failed; incomplete initiation. | |
| Recycle 1 | 90/2.0 | 63/1st hr/7.5%/2450 1.5th hr/10.5%/2500 2.3nd hr/11.0%/2500 19th hr/10.5%/2780 | 153 mcg Catalyst rinsed THF |
| Recycle 2 | 90/4.5 | 65/1st hr/4.4%/3040 1.5th hr/5.0%/2891 20th hr/15%/2882 | Catalyst rinsed THF |
| Recycle 3 | 90/36.0 | 60/2nd hr/5%/2891 3rd hr/4%/2852 | 122 mcg Catalyst rinsed THF |
| Recycle 4 | 90/14.0 | 60/1st hr/11%/2800 2nd hr/22%/2852 | 119 mcg Catalyst rinsed THF Added 2 g CF$_3$CO$_2$H. |
| Recycle 5 | 90/4.0 | 62/1st hr/2%/1300 | 175 mcg Catalyst rinsed THF |
| Recycle 6 | 90/12.0 | 67/1st hr/5%/1300 2nd hr/13.6%/1300 3rd hr/13.5%/1300 | See footnote (1). Catalyst rinsed THF |
| Recycle 7 | 90/12.0 | 60/1st hr/5%/1300 2nd hr/11%/1300 | See footnote (2). Catalyst rinsed THF |
| Recycle 8 | 90/12.0 | 60/1st hr/4.5%/1300 2nd hr/6.9%/1384 3rd hr/7.0%/1300 5th hr/4.5%/1300 | See footnote (3). Reaction stopped. |
| EXAMPLE 7 | | | |
| Virgin | 85/3.0 | 8/1st hr/2.0%/3000 | Catalyst rinsed THF |
| Recycle | 85/16.0 | 7/1st hr/1.5%/low $M_n$ 2nd hr/6.5%/ low $m_n$ 4.5th hr/2.0%/ low $m_n$ | Catalysts rinsed THF |
| Recycle 2 | 85/16.0 | 7-23/2nd hr/2.5%/3000 7th hr/4.0%/3000 | Catalyst rinsed THF |
| Recycle 3 | 85/16 | 7-9/1st hr/6.0%/3000 | Reaction stopped |
| EXAMPLE 8 | | | |
| Virgin | 86/16.0 | 6/1st hr/<1.%/ low $M_n$ 30/5th hr/2.5%/ low $M_n$ | 200 mcg Catalyst rinsed THF |
| Recycle 1 | 86/19.0 | 6/1st hr/7%/3200 2.5 hr/10%/3200 3.5 hr/8%/3200 | 114 mcg Catalysts rinsed THF |
| Recycle 2 | 86/4.0 | 8/1st hr/7%/3200 | 121 mcg Catalyst rinsed THF Added 0.01 g water. |
| Recycle 3 | 86/13.0 | 6/0.5 hr/3.0%/3000 1.0 hr/4.6%/3000 | 143 mcg Catalyst rinsed THF |
| Recycle 4 | 86/17.0 | 6/0.5 hr/16.0%/3200 1.2 hr/14.0%/3200 | 144 mcg Reaction stopped. |
| EXAMPLE 9 | | | |
| Virgin | 85/16.0 | 51/0.5 hr/4.8%/ low $M_n$ 1.5 hr/6.5%/ low $M_n$ 4.0 hr/7.3%/ low $M_n$ | 231 mcg Catalyst rinsed THF |
| Recycle 1 | 86/18.0 | 56/0.5 hr/7.2%/2350 1st hr/7.8%/2350 3rd hr/7.2%/2350 5th hr/9.7%/2350 | 81 mcg Catalyst rinsed THF |
| Recycle 2 | 86/17.0 | 54/0.5 hr/26%/3200 | 131 mcg Catalyst rinsed THF Added 0.025 g water. |
| Recycle 3 | 86/4.0 | 56/0.5 hr/17%/3200 | Catalyst rinsed THF Added 0.049 g water. |
| Recycle 4 | 86/2.5 | 59/0.5 hr/6.5%/3000 | 149 mcg Reaction Terminated |

Footnotes:
(1) Agitation lost during INITIATION.
(2) No agitation during INITIATION or PROPAGATION.
(3) No agitation during INITIATION.

EXAMPLE 10

Continuous Operation: Feed Rate of THF = 0.9 mL/Minute
Catalyst: 120.13 g of 70% PFIEP-SO$_3$H/30% PFIEP-CO$_2$H

| Elapsed Cumulative Time, Hours | Water Content of THF, mcg | Conversion To PTMEG, % by Weight | Number Average Molecular Weight. $M_n$ | moles of PTMEG |
|---|---|---|---|---|

Reactor Temperature = 65° C.

Continuous Operation: Feed Rate of THF = 0.9 mL/Minute
Catalyst: 120.13 g of 70% PFIEP-SO₃H/30% PFIEP-CO2H

| Elapsed Cumulative Time, Hours | Water Content of THF, mcg | Conversion To PTMEG, % by Weight | Number Average Molecular Weight, $M_n$ | moles of PTMEG |
|---|---|---|---|---|
| 0 | 530 | 0 | 0 | 0 |
| 24 | 580 | 1.60 | 800 | 0.0104 |
| 41 | 630 | 1.50 | 717 | 0.0181 |
| 47 | 630 | 1.13 | 749 | 0.0201 |
| 65 | 491 | 2.70 | 792 | 0.0334 |
| 72 | 500 | 2.20 | 815 | 0.0375 |
| 88 | 606 | 3.20 | 880 | 0.0501 |
| 96 | 935 | 3.20 | 904 | 0.0562 |
| 117 | — | 4.00 | 940 | 0.0755 |
| 144 | 658 | 4.00 | 1088 | 0.0969 |
| 162 | 539 | 4.00 | 1004 | 0.1124 |
| 167 | 539 | 5.15 | 1028 | 0.1178 |
| 187 | 409 | 8.90 | 1200 | 0.1498 |
| 191 | 409 | 7.40 | 1112 | 0.1555 |
| 210 | 409 | 11.90 | 1080 | 0.2007 |
| 214 | 409 | 15.10 | 1587 | 0.2089 |
| 234 | 376 | 13.90 | 1572 | 0.2471 |
| 238 | 604 | 8.00 | 1575 | 0.2515 |
| 239 | 604 | 7.00 | 2124 | 0.2522 |
| 257 | 657 | 9.80 | 1956 | 0.2717 |

Reactor temperature was 68° C. at 257 hours. Reactor temperature dropped to 61° C. by 262 hours and maintained at that temperature until hour 689 at termination of run.

| | | | | |
|---|---|---|---|---|
| 262 | 657 | 9.80 | 2058 | 0.2768 |
| 304 | 550 | 9.00 | 2948 | 0.3045 |
| 334 | 518 | 7.00 | 3203 | 0.3187 |
| 355 | 578 | 11.75 | 1931 | 0.3463 |
| 359 | 578 | 13.40 | 2003 | 0.3521 |
| 383 | — | 11.00 | 2641 | 0.3737 |
| 402 | 349 | 12.30 | 3561 | 0.3879 |
| 407 | 447 | 14.07 | 3819 | 0.3919 |
| 450 | — | 0.03 | 9918 | 0.3919 |
| 501 | — | 14.80 | 4636 | 0.4271 |
| 521 | — | 3.80 | 2786 | 0.4330 |
| 525 | — | 3.90 | 3113 | 0.4341 |
| 545 | — | 6.00 | 3500 | 0.4415 |
| 549 | — | 12.80 | 2760 | 0.4455 |
| 570 | — | 47.10 | 3416 | 0.5080 |
| 689 | — | 1.20 | 3480 | 0.5169 |

We claim:

1. A process for the manufacture of poly(tetramethylene ether) glycols of number average molecular weight 250 to 4,000 by polymerization of tetrahydrofuran containing 10 to 300 ppm water in the presence of 5 to 45 percent of the weight of tetrahydrofuran charged of pelletred perfluorinated ion, acidic ion exchange resin catalyst consisting of a blend of
   a) melt-fabricable polymer having sulfonyl functional groups, which is a polymer having a fluorinated hydrocarbon backbone chain to which are attached the functional groups or pendant side chains which in turn carry the functional groups, the pendant side chains containing,

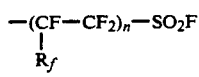

groups, wherein $R_f$ is F, Cl, or a C-1 to C-10 perfluoroalkyl radical, and n is an integer from 1 to 5 with the functional group in the side chains of the polymer present in terminal

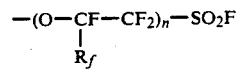

groups, and
   b) a melt-fabricable polymer having carboxylic functional groups, having a fluorinated hydrocarbon backbone chain to which are attached the functional groups or pendant side chains which carry the functional groups, the pendant side chains containing,

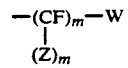

groups, wherein Z is F or CF₃, m is 1 to 12, and W is —COOR, —CF₂COOR or —CN, where R is lower alkyl with the functional group in the side chains of the polymer present in terminal

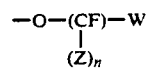

groups; and
   c) melt blending 40-95 percent of the melt-fabricable polymer from a) above with 60-5 percent of the melt-fabricatable polymer from b) above, and up to 80 percent of an inert filler selected from polytetrafluoroethylene, polychlorotrifluoroethylene or copolymers of tetrafluoroethylene or chlorotrifluoroethylene with one or more of hexafluoropropylene or a perfluoroalkyl vinyl ether wherein the alkyl group contains from 1 to 6 carbon atoms or any combination thereof; pelletizing the resulting polymer, and
   d) converting the pelletizeable melt-fabricable polymer from c) by hydrolyzing and then acidifying followed by reducing the water content of the polymer to 1,000 to 2,000 parts per million, said tetrahydrofuran polymerization process being carried out with stirring or agitation at a temperature from 0° to 65° C. for a period of time of 2 to 60 hours until the desired degree of polymerization has been reached followed by separation of the product poly(tetramethylene ether) glycol from the catalyst.

2. The process of claim 1 wherein the moisture content of the catalyst, prior to use, has been reduced to 1,000 to 2,000 ppm by over drying the catalyst at about 90° C. for about 8 hours under a pressure between 0.1-100 mm Hg (absolute) followed by mixing with tetrahydrofuran containing from 50 to 300 ppm water and heating under nitrogen at a pressure of from 0.1 to 10 mm Hg at between 85° to 150° C. for at least 3 hours under conditions that prevent polymerization of tetrahydrofuran.

3. The process of claim 1 wherein the moisture content of the catalyst, prior to use, has been reduced to from 1,000 to 2,000 ppm by repeated leaching of the catalyst with dry tetrahydrofuran containing less than 100 ppm water at temperatures ranging from 0° to 90° C. until the water concentration in the leachant tetrahydrofuran is reduced to below 100 ppm and the residual water content in the leached catalyst is 1,000 to 2,000 ppm.

4. The process of claim 1 wherein the moisture content of the catalyst, prior to use, has been reduced to from 1,000 to 2,000 ppm by oven drying the catalyst at 140° to 180° C. under a pressure of 0.1 to 10 mm Hg (absolute) in the presence of 0.5 to 50 parts of trimethyl formate per part of catalyst to convert water in the catalyst to methyl formate, followed by further heating of the catalyst under vacuum in an oven for at least 8 hours to volatilize out the last traces of trimethyl orthoformate and methyl formate and the residual content of water in the catalyst is from 1,000 to 2,000 ppm.

5. The process of claim 1 wherein the moisture of the catalyst, prior to use, has been reduced to 1,000 to 2,000 ppm by extractive distillation of water from the catalyst in the presence of 10 to 20 parts tetrahydrofuran per part of catalyst by weight, whereby wet catalyst is mixed with tetrahydrofuran and the tetrahydrofuran/water mixture or azeotrope is distilled off to yield a catalyst with residual moisture remaining in the catalyst ranging from 1,000 to 2,000 ppm.

6. A continuous process for the manufacture of poly(tetramethylene ether) glycols of number average molecular weight 250 to 4,000 by feeding 0.1 to 1.0 g per hour of tegrahydrofuran, per gram of the pelleted perfluorinated ion exchange resin of claim 1, said tetrahydrofuran containing less than 1000 ppm water for a hold-up time of from 4 to 40 hours, operating at temperatures ranging from 5° to 70° C., followed by recovery of the effluent and further processing under reduced pressure to remove excess tetrahydrofuran and traces of volatilizes from the product poly(tetramethylene ether) glycol.

7. The process of claim 6 wherein the moisture content of the catalyst, prior to use, has been reduced to from 1,000 to 2,000 ppm by over drying the catalyst at above 100° C. for about 8 hours under a pressure between 0.1-100 mm Hg (absolute) followed by mixing with tetrahydrofuran containing from 50 to 300 ppm water and heating under nitrogen at a pressure from 0.1 to 10 mm Hg (absolute) for at least 3 hours under conditions that prevent polymerization of tetrahydrofuran.

8. The process of claim 6 wherein the moisture content of the catalyst, prior to use, has been reduced from 1,000 to 2,000 ppm by repeated leaching of the catalyst with dry tetrahydrofuran containing less than 100 ppm water at temperatures ranging from 0° to 90° C. until the water concentration in the leachant tetrahydrofuran is reduced to below 100 ppm and the residual water content in the catalyst is from 1,000 to 2,000 ppm.

9. The process of claim 6 wherein the moisture content of the catalyst, prior to use, has been reduced to from 1,000 to 2,000 ppm by oven drying the catalyst at 140° to 180° C. under a pressure of 0.1 to 10 mm Hg (absolute) in the presence of 0.5 to 50 parts of trimethyl formate per part of catalyst to convert water in the catalyst to methyl formate, followed by further heating of the catalyst under vacuum in an oven for at least 8 hours to volatilize out the last traces of trimethyl orthoformate and methyl formate and the residual water content in the catalyst is from 1,000 to 2,000 ppm.

10. The process of claim 6 wherein the moisture content of the catalyst, prior to use, has been reduced to 1,000 to 2,000 ppm by extractive distillation of water from the catalyst in the presence of 10 to 20 parts of tetrahydrofuran per part of catalyst by weight, whereby wet catalyst is mixed with tetrahydrofuran and the azeotrope of the tetrahydrofuran/water mixture is distilled off to yield catalyst with residual moisture remaining in the catalyst ranging from 1,000 to 2,000 ppm.

* * * * *